United States Patent [19]

Moucharafieh et al.

[11] Patent Number: 5,362,705
[45] Date of Patent: Nov. 8, 1994

[54] HERBICIDAL FORMULATIONS CONTAINING N-PHOSPHONOMETHYLGLYCINE AND ALKYL PHENOL POLYOXYALKYLENE CARBOXYLIC ACID SURFACTANT

[75] Inventors: Nadim C. Moucharafieh, El Sobrante; Kang-Chi Lin, Lafayette; James L. Ahle, Novato, all of Calif.

[73] Assignee: Zeneca Ltd., London, United Kingdom

[21] Appl. No.: 90,583

[22] Filed: Jul. 13, 1993

[51] Int. Cl.$^5$ .................... A01N 25/30; A01N 57/12
[52] U.S. Cl. .................... 504/206; 504/116; 71/DIG. 1
[58] Field of Search ............ 504/116, 206; 71/DIG. 1

[56] References Cited

U.S. PATENT DOCUMENTS

| | | | |
|---|---|---|---|
| 3,799,758 | 3/1974 | Franz | 504/206 |
| 4,159,901 | 7/1979 | Beestman et al. | 71/86 |
| 4,182,621 | 1/1980 | Ogata et al. | 71/76 |
| 4,312,662 | 1/1982 | Gaertner | 560/132 |
| 4,931,080 | 6/1990 | Chan et al. | 71/86 |
| 5,047,079 | 9/1991 | Djafar et al. | 71/DIG. 1 |
| 5,118,338 | 6/1992 | Moller | 71/86 |
| 5,180,414 | 1/1993 | Darchy et al. | 504/206 |
| 5,196,044 | 3/1993 | Caulder et al. | 504/127 |

FOREIGN PATENT DOCUMENTS

| | | |
|---|---|---|
| 378985 | 7/1990 | European Pat. Off. . |
| 472310 | 2/1992 | European Pat. Off. . |
| 531269 | 3/1993 | European Pat. Off. . |

OTHER PUBLICATIONS

Wyrill et al., Weed Science 25, 275 (1977).
Grossbard et al., The Herbicide Glyphosate (Butterworths, London, 1985), pp. 223–225.

*Primary Examiner*—Allen J. Robinson
*Assistant Examiner*—Brian Bembenick
*Attorney, Agent, or Firm*—Joel G. Ackerman

[57] ABSTRACT

Herbicidal compositions contain N-phosphonomethyglycine and alkyl phenol polyoxyalkylene surfactant which contains from about 50 to about 90 weight percent of alkyl phenol polyoxyethylene carboxylic acid.

20 Claims, No Drawings

HERBICIDAL FORMULATIONS CONTAINING N-PHOSPHONOMETHYLGLYCINE AND ALKYL PHENOL POLYOXYALKYLENE CARBOXYLIC ACID SURFACTANT

BACKGROUND OF THE INVENTION

This invention relates to novel herbicidal compositions, particularly aqueous solutions, containing the herbicide N-phosphonomethylyglycine (also known as glyphosate) and an alkyl phenol polyoxyalkylene carboxylic acid-containing surfactant.

N-phosphonomethylglycine, as well as analogous compounds including salts, and the herbicidal properties and formulations containing them, are described in numerous patents, such as U.S. Pat. No. 3,799,758. This patent describes a number of compositions containing N-phosphonomethylglycine and analogous compounds and discloses that the incorporation of a surface-active agent into such compositions "greatly enhances their efficiency". A number of surface-active agents are disclosed in that patent.

The patent also mentions that because N-phosphonomethylglycine itself is relatively insoluble in water, it is generally preferred to utilize the more readily soluble derivatives of N-phosphonomethylglycine, including metal salts and salts of N-phosphonomethylglycine and strong acids, namely those having a pK of 2.5 or less, such as hydrochloric, sulfuric, phosphoric, trifluoracetic, trichloracetic, and the like.

A number of subsequent patents and patent applications describe in more detail particular surfactants which may be used with N-phosphonomethylglycine or its salts. For instance, U.S. Pat. No. 5,180,414 describes compositions of N-phosphonomethylglycine containing certain alkyl polyoxyethylene phosphoric acid ester surfactants. European Patent Application 290,416 describes compositions containing N-phosphonomethylglycine or its salts and an alkoxylated amine having at the most 12 alkoxy groups per molecule. European Patent Application 472,310 describes new surfactant compositions for use with pesticides, including glyphosate, which comprise a polyoxyalkylene alkyl amine containing at least about 7 moles of an oxyalkylene group combined with a second compound which has the property of reducing eye irritantcy. Such eye irritant-reducing compounds include sulfated polyoxyalkylene alkyl phenols, polyoxyalkylene alcohol sulfates, mono- and di-(polyoxyalkylene alcohol)phosphates, mono- and di-(polyoxyalkylene alkyl phenol)phosphates, polyoxyalkylene alkyl phenol carboxylates and polyoxyalkylene carboxylates.

It is an object of the present invention to provide new phosphonomethylglycine-containing compositions, particularly aqueous solutions of N-phosphonomethylglycine which may be readily used for herbicidal application and control of undesirable plants.

SUMMARY OF THE INVENTION

This invention comprises a herbicidal composition comprising:
a) From about 0.1 to about 1.5 weight percent N-phosphonomethylglycine;
b) from about 0.1 to about 5 weight percent of an alkyl phenol polyoxyethylene surfactant containing from about 50 to about 90 weight percent of an alkyl phenol polyoxyethylene carboxylic acid;
c) the remainder comprising water, and a method for controlling undesirable vegetation using such a composition.

DETAILED DESCRIPTION OF THE INVENTION

As mentioned above, this invention comprises an aqueous solution containing from about 0.1 to about 1.5 weight percent N-phosphonomethylglycine or glyphosate, and from about 0.1 to about 5 weight percent of an alkyl phenol polyoxyethylene surfactant having a high anionic content of an alkyl phenol polyoxyethylene carboxylic acid, the remainder of the composition comprising water.

Such a surfactant has been found to be surprisingly effective for use in aqueous solutions of glyphosate. The reason that this effect is surprising is that notwithstanding the comments in U.S. Pat. No. 3,799,758 that anionic, cationic and nonionic surfactants can be used with equal facility, it is well known in the art that anionic surfactants tend to be less effective than either cationic or nonionic surfactants. See, for example, Wyrill et al., "Glyphosate Toxicity to Common Milkweed and Hemp Dogbane as Influenced by Surfactants", *Weed Science*, Vol. 25, #3, pp. 275–287 (particularly p. 281) (May 1977).

The surfactants which have been found useful in compositions according to this invention contain from about 50 to about 90 weight percent of an alkyl phenol polyoxyethylene carboxylic acid, namely, a compound having the formula

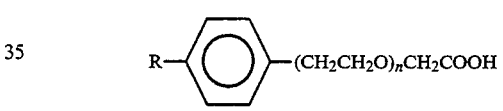

in which R is a $C_8$—$C_{20}$ alkyl group, most preferably $C_8$—$C_9$ alkyl group, and n is a value of from 3 to 100. In general, the surfactant overall is a nonionic alkyl phenol polyoxyethylene surfactant in which a major portion of the composition has been converted from the nonionic alcohol or ether to the weak electrolyte anionic carboxylic acid.

The overall content of alkyl phenol polyoxyethylene carboxylic acid surfactant in the compositions of this invention is from about 0.1 to about 5, preferably from about 0.5 to about 1, weight percent, and the content of N-phosphonomethylglycine is from about 0.1 to about 1.5, preferably from about 0.3 to about 1 weight percent, with the alkyl phenol polyoxyethylene carboxylic acid surfactant and N-phosphonomethylglycine preferably being present in a 1:1 molar ratio.

In a further preferred embodiment, the compositions of this invention may also contain from about 0.1 to about 5, preferably from about 0.5 to about 2 weight percent, of a humectant and optionally from about 0.1 to about 5, preferably from about 0.3 to about 1, weight percent of a wetting agent, particularly an alkyl polyglycoside wetting agent. The preferred humectant in such compositions is a glycol, preferably glycerol. Others which may be used are sorbitol, ethylene glycol and propylene glycol. The preferred alkyl polyglycoside wetting agents are AL-2042 and Atplus 258, obtainable from Imperial Chemical Industries PLC and its subsidiaries. Other wetting agents which may be used in these compositions include alkyl phenol ethoxylates, fatty acid polyglycol ethers, ethylene oxide-propylene oxide copolymers, sorbitol esters, and sucrose esters.

Compositions of this invention may be prepared in one of several ways.

Such compositions may be prepared by simply mixing the requisite amounts of N-phosphonomethylglycine, alkyl phenol polyoxyethylene surfactant (containing the alkyl phenol polyoxyalkylene carboxylic acid), water, and such other additives as may be included. N-phosphonomethylglycine is known to have limited solubility in water; in this manner a ready-to-use composition containing up to about 1.5 weight percent N-phosphonomethylglycine may be prepared.

An alternate method would be to prepare a concentrate containing N-phosphonomethylglycine or one of its more water-soluble derivatives such as an alkali metal or amine salt with the alkyl phenol polyoxyethylene surfactant (containing the alkyl phenol polyoxyethylene carboxylic acid) to form a concentrate, and then subsequently dissolving said concentrate in water. The additional materials, such as humectant and/or wetting agent, may be added either to the concentrate or to the aqueous solution of N-phosphonomethylglycine prepared from the concentrate.

In addition to the surprising effect of an anionic surfactant, it was also surprising to have found that these surfactants can be used with N-phosphonomethylglycine because U.S. Pat. No. 3,799,758 refers to salts of N-phosphonomethylglycine with the strong acids, namely those having a pK of 2.5 or less, whereas the carboxylates of the present invention have a pK of higher than 2.5, generally 4 or above.

It has also been found that compositions according to this invention show improved results against certain weeds, particularly perennial weeds, in comparison to the commercial glyphosate formulation sold as Roundup® Ready-To-Use. This is surprising because Roundup contains the isopropylamine salt of glyphosate, which is more active as a herbicide than glyphosate itself.

Examples of alkyl phenol polyoxyethylene surfactants containing the requisite high percentage content of alkyl phenol polyoxyethylene carboxylic acid, are Sandopan MA-18 (R=nonyl, n=9) and MA-200 (R=nonyl, n=100), available from Sandoz, and Emcol CNP-40 (R=n-nonyl, n=4), CNP-100 (R=n-nonyl, n=8), 110 (R=n-nonyl, n=50% 8 and 50% 10), and CNP-120 (R=n-nonyl, n=10), available from Witco Corporation.

The following represent examples of the preparation of compositions according to this invention.

EXAMPLE 1

Four grams of Sandopan MA-18 (molecular weight 674.87) (0.0059 mole) was dissolved in 100 ml water; then 1 gram of solid N-phosphomethylglycine (0.0059 mole) was added to the water. The phosphonomethylglycine solid dissolved completely in the water.

EXAMPLE 2

Similarly to Example 1, a solution was prepared containing of N-phosphonomethylglycine and Sandopan MA-18 in water, to which was added 0.5 weight percent AL-2042 wetting agent.

EXAMPLE 3

Similarly to Example 1, a solution was prepared containing N-phosphonomethylglycine and Sandopan MA-18 and 0.5 percent LODOSE, an ethoxylated amine wetting agent.

EXAMPLE 4

Similarly to Example 1, a solution was prepared containing N-phosphonomethylglycine and Sandopan MA-200 in a 1:1 molar matio.

EXAMPLE 5

Similarly to Examples 1 to 4, a solution was prepared containing N-phosphonomethylglycine and Sandopan MA-200 in a 1:1 molar ratio, and 0.5 weight percent AL-2042.

EXAMPLE 6

Similarly to the above, a solution was prepared containing N-phosphonomethylglycine and Sandopan MA-18 in a 1:1 weight ratio, and 5 weight percent glycerol.

EXAMPLE 7

Similarly to Example 1, a solution was prepared using 0.77 weight percent technical N-phosphonomethylglycine (90% purity; 0.69 weight percent active ingredient), 0.77 weight percent Sandopan MA-18, 2.00 weight percent glycerol, 0.50 weight percent Atplus 258 wetting agent, and 95.96 weight percent water.

EXAMPLE 8

Similarly to the above, a solution was prepared using 0.75 weight percent technical grade N-phosphonomethylglycine (90% purity; 0,675 weight percent active ingredient), 1 weight percent Sandopan MA-18 and 0.5 weight percent AL-2042.

EXAMPLE 9

Similarly to the above, a solution is prepared having the contents as follows:

| Ingredient | Grams | Weight Percent |
|---|---|---|
| N-phosphonomethylglycine (technical grade, 90% purity) | 30.8 | 0.77 (0.71) |
| Sandopan MA-18 | 30.8 | 0.77 |
| Glycerol | 80.0 | 2.00 |
| Atplus 258 | 20.0 | 0.50 |
| Proxel BD Biostat | 12.0 | 0.30 |
| Water | 3826.4 | 95.66 |
| Totals | 4,000.0 | 100.00 |

The compositions described in Examples 1 through 8 were evaluated for herbicidal activity as follows:

The following weeds were used in the tests:

*Lolium perenne* (perennial ryegrass, LOLPE), *Abutilon theophrasti* (velvetleaf, ABUTH), *Ipomoea hedera* (ivyleaf morningglory, IPOHE), *Cynodon dactylon* (bermudagrass, CYNDA), *Agropyron repens* (quackgrass, AGRRE), *Convolvulus arvensis* (field bindweed, CONAR) and *Cyperus rotundus* (purple nutsedge, CYPRO).

The compositions were applied post-emergence at four application rates, based on N-phosphonomethylglycine content, using three replications. The spray volume was 25 gallons per acre (234 l/ha); plants were treated 20–24 days after the plants had been seeded (Ready-To-Use formulations were sprayed at 3 or 4 spray volumes). Ratings were taken at 14 and 25–29 days after application, with the plants being visually rated on a scale of from 0 to 100 in which 0 represented no effect as compared to an untreated control flat, and 100 represented complete kill. Regrowth ratings on perennial weeds were taken at 49 days after application.

Table 1 shows results of testing Examples 1 through 6 and 8 with readings taken at 25-29 days after treatment. Table 2 shows results taken at 49 days after treatment with Example 7, in comparison with Roundup Ready-To-Use at three spray rates.

TABLE 1

| Example | | % Control, 25-29 DAT | | |
|---|---|---|---|---|
| | | LOLPE | ABUTH | IPOHE |
| | Rate, lb/acre PMG | | | |
| 1 | 0.125 | 0 | 7 | 13 |
| | 0.250 | 3 | 27 | 27 |
| | 0.500 | 17 | 87 | 50 |
| | 1.00 | 89 | 99 | 80 |
| 2 | 0.125 | 40 | 10 | 23 |
| | 0.250 | 57 | 70 | 57 |
| | 0.500 | 99 | 95 | 91 |
| | 1.000 | 100 | 100 | 97 |
| 3 | 0.125 | 33 | 47 | 40 |
| | 0.250 | 77 | 73 | 63 |
| | 0.500 | 99 | 98 | 77 |
| | 1.000 | 100 | 99 | 96 |
| 4 | 0.125 | 10 | 17 | 17 |
| | 0.250 | 20 | 47 | 33 |
| | 0.500 | 73 | 87 | 53 |
| | 1.000 | 97 | 100 | 75 |
| 5 | 0.125 | 37 | 33 | 33 |
| | 0.250 | 83 | 77 | 63 |
| | 0.500 | 98 | 92 | 70 |
| | 1.000 | 100 | 99 | 93 |
| 6 | 0.125 | 57 | 70 | 30 |
| | 0.250 | 77 | 97 | 47 |
| | 0.500 | 99 | 100 | 70 |
| | 1.000 | 100 | 100 | 93 |
| | Rate, gal/acre | | | |
| 8 | 12.5 | 98 | 94 | 57 |
| | 25 | 100 | 96 | 67 |
| | 50 | 100 | 100 | 95 |
| | 100 | 100 | 100 | 99 |

TABLE 2

| Example | Rate, gal/acre | % Control of Regrowth | | | |
|---|---|---|---|---|---|
| | | CYNDA | AGRRE | CONAR | CYPRO |
| 7 | 10 | 100 | 93 | 10 | 100 |
| | 20 | 100 | 100 | 40 | 100 |
| | 40 | 100 | 100 | 63 | 100 |
| Roundup Ready-To-Use | 10 | 0 | 0 | 13 | 67 |
| | 20 | 90 | 50 | 20 | 99 |
| | 40 | 100 | 100 | 67 | 100 |

What is claimed is:

1. A herbicidal composition comprising
 a) from about 0.1 to about 1.5 weight percent N-phosphonomethylglycine;
 b) from about 0.1 to about 5 weight percent of an alkyl phenol polyoxyethylene surfactant containing from about 50 to about 90 weight percent alkyl phenol polyoxyethylene carboxylic acid;
 c) the remainder comprising water.

2. A composition according to claim 1 in which the alkyl phenol polyoxyethylene carboxylic acid has the formula

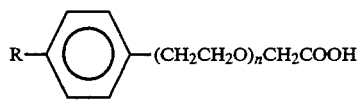

in which R is a $C_8$—$C_{20}$ alkyl group, and n is an integer from to 100.

3. A composition according to claim 1 further comprising from about 0.1 to about 5 weight percent of a humectant.

4. A composition according to claim 3 in which the humectant is a glycol.

5. A composition according to claim 4 in which the humectant is glycerol.

6. A composition according to claim 3 further comprising from about 0.5 to about 2 weight percent of a humectant.

7. A composition according to claim 1 further comprising from about 0.1 to about 5 weight percent of a wetting agent.

8. A composition according to claim 7 further comprising from about 0.3 to about 1 weight percent of a wetting agent.

9. A composition according to claim 7 in which the wetting agent is an alkyl polyglycoside or a sucrose ester.

10. A composition according to claim 1 comprising from about 0.5 to about 1 weight percent N-phosphonomethylglycine, and from 0.5 to about 2 weight percent surfactant containing alkyl phenol polyoxyethylene carboxylic acid.

11. A composition according to claim 1 in which the molar ratio of N-phosphonomethylglycine to surfactant is about 1:1.

12. A composition according to claim 1 in which the alkyl phenol polyoxyethylene carboxylic acid has a pK of greater than or equal to 4.

13. A composition according to claim 1 consisting essentially of
 (a) from about 0.1 to about 1.5 weight percent N-phosphonomethylglycine
 (b) from about 0.1 to about 5 weight percent of an alkyl phenol polyoxyethylene surfactant containing from about 50 to about 90 weight percent of an alkyl phenol polyoxyethylene carboxylic acid having the formula

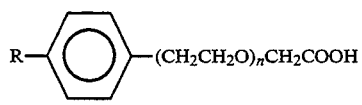

in which R is a $C_8$ or $C_9$ alkyl group and n is an integer from 3 to 100;
 (c) from about 0.1 to about 5 weight percent of a glycol humectant;
 (d) optionally from about 0.5 to about 5 weight percent of an alkyl polyglycoside wetting agent;
 (e) the remainder water.

14. A composition according to claim 13 comprising from about 0.5 to about 1 weight percent N-phosphonomethylglycine, from about 0.3 to about 1 weight percent alkyl phenol polyoxyalkylene surfactant, from about 0.5 to about 2 weight percent humectant and optionally from about 0.3 to about 1 weight percent wetting agent.

15. A composition according to claim 13 in which the humectant is glycerol.

16. A composition according to claim 14 in which the humectant is glycerol.

17. A composition according to claim 13 in which the molar ratio of N-phosphonomethylglycine to surfactant is about 1:1.

18. A composition according to claim 14 in which the molar ratio of N-phosphonomethylglycine to surfactant is about 1:1.

19. A method for controlling undesirable vegetation comprising applying to said vegetation or the locus thereof, a herbicidally effective amount of a composition according to claim 1.

20. A method for controlling undesirable vegetation comprising applying to said vegetation or the locus thereof, a herbicidally effective amount of a composition according to claim 14.

* * * * *

UNITED STATES PATENT AND TRADEMARK OFFICE
CERTIFICATE OF CORRECTION

PATENT NO.  : 5,362,705
DATED       : November 8, 1994
INVENTOR(S) : Nadim C. MOUCHARAFIEH, Kang-Chi LIN, and
              James L. AHLE It is certified that error appears in the above-identified patent and that said Letters Patent is hereby corrected as shown below:

Column 2, line 35,

Column 5, line 65, and

Column 6, line 45 the formula should read 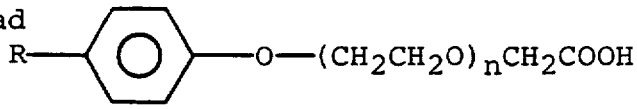

Signed and Sealed this

Twenty-sixth Day of September, 1995

Attest:

BRUCE LEHMAN

Attesting Officer

Commissioner of Patents and Trademarks